United States Patent
Msika et al.

(10) Patent No.: US 11,026,880 B2
(45) Date of Patent: Jun. 8, 2021

(54) EXTRACT OF PASSIONFLOWER SEEDS AND COSMETIC, PHARMACEUTICAL, DERMATOLOGICAL AND NUTRACEUTICAL COMPOSITIONS COMPRISING SAME

(71) Applicant: Laboratoires Expanscience, Courbevoie (FR)

(72) Inventors: Philippe Msika, Versailles (FR); Sophie Leclere-Bienfait, Dreux (FR); Sebastien Debrock, St Martin de Nigelles (FR); Stephanie Bredif, Croisilles (FR); Sebastien Garnier, Opio (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 890 days.

(21) Appl. No.: 14/652,449

(22) PCT Filed: Dec. 18, 2013

(86) PCT No.: PCT/EP2013/077065
§ 371 (c)(1),
(2) Date: Oct. 14, 2015

(87) PCT Pub. No.: WO2014/095983
PCT Pub. Date: Jun. 26, 2014

(65) Prior Publication Data
US 2016/0074312 A1 Mar. 17, 2016

(30) Foreign Application Priority Data
Dec. 18, 2012 (FR) ........................ 1262234

(51) Int. Cl.
| | | |
|---|---|---|
| *A61K 8/97* | (2017.01) | |
| *A61Q 19/08* | (2006.01) | |
| *A61K 36/185* | (2006.01) | |
| *A61Q 19/06* | (2006.01) | |
| *A61Q 17/00* | (2006.01) | |
| *A61K 8/60* | (2006.01) | |
| *A61K 8/64* | (2006.01) | |
| *A61K 45/06* | (2006.01) | |
| *A61Q 5/02* | (2006.01) | |
| *A61Q 5/12* | (2006.01) | |
| *A61Q 17/04* | (2006.01) | |
| *A61Q 19/00* | (2006.01) | |
| *A61Q 19/02* | (2006.01) | |
| *A61Q 7/00* | (2006.01) | |

(52) U.S. Cl.
CPC ............... *A61K 8/97* (2013.01); *A61K 8/60* (2013.01); *A61K 8/645* (2013.01); *A61K 36/185* (2013.01); *A61K 45/06* (2013.01); *A61Q 5/02* (2013.01); *A61Q 5/12* (2013.01); *A61Q 17/00* (2013.01); *A61Q 17/04* (2013.01); *A61Q 19/005* (2013.01); *A61Q 19/007* (2013.01); *A61Q 19/02* (2013.01); *A61Q 19/06* (2013.01); *A61Q 19/08* (2013.01); *A61K 2236/15* (2013.01); *A61K 2236/19* (2013.01); *A61Q 7/00* (2013.01)

(58) Field of Classification Search
None
See application file for complete search history.

(56) References Cited

U.S. PATENT DOCUMENTS

2012/0004322 A1  1/2012  Matsui et al.

FOREIGN PATENT DOCUMENTS

| FR | 955344 | 1/1950 |
|---|---|---|
| FR | 958525 | 3/1950 |
| FR | 1061047 | 4/1954 |
| FR | 1061051 | 4/1954 |
| FR | 1061055 | 4/1954 |
| FR | 2822821 | 10/2002 |
| FR | 2857596 | 1/2005 |
| JP | 2007099751 | 4/2007 |
| JP | 2009102298 | 5/2009 |

(Continued)

OTHER PUBLICATIONS

International Search Report, dated Feb. 24, 2014, Application No. PCT/EP2013/077065.

(Continued)

*Primary Examiner* — Terry A McKelvey
*Assistant Examiner* — Catheryne Chen
(74) *Attorney, Agent, or Firm* — Womble Bond Dickinson (US) LLP

(57) ABSTRACT

The invention relates to a composition comprising an extract of passionflower seeds, and preferentially *Passiflora edulis* seeds. The composition is advantageously cosmetic, pharmaceutical, dermatological or nutraceutical. The subject matter of the invention is also a process for extracting an extract of passionflower seeds and preferentially *Passiflora edulis* seeds, and also the extract which can be obtained by means of said process. The invention also relates to such a composition or such an extract for use in the prevention or treatment of disorders or pathological conditions of the skin, of the mucous membranes or of the skin appendages, for use in the prevention or treatment of vascular disorders, for use for combating oxidative stress, or else for use in the prevention or treatment of adipose tissue modifications. Finally, the invention relates to a cosmetic care process for the skin, the skin appendages or the mucous membranes, with a view to improving, the condition thereof or the appearance thereof, consisting in administering such a composition or such an extract.

29 Claims, No Drawings

(56) References Cited

FOREIGN PATENT DOCUMENTS

| WO | WO-0121150 | 3/2001 |
|----|-----------|--------|
| WO | WO-0121605 | 3/2001 |
| WO | WO-0152837 | 7/2001 |
| WO | WO-0206205 | 1/2002 |
| WO | WO-2004012496 | 2/2004 |
| WO | WO-2004012752 | 2/2004 |
| WO | WO-2004016106 | 2/2004 |
| WO | WO-2004050052 | 6/2004 |
| WO | WO-2004050079 | 6/2004 |
| WO | WO-2004057439 | 7/2004 |
| WO | WO-2004112741 | 12/2004 |
| WO | WO-2004112742 | 12/2004 |
| WO | WO-2005102259 | 11/2005 |
| WO | WO-2005105123 | 11/2005 |
| WO | WO-2005115421 | 12/2005 |
| WO | WO-2008080974 | 7/2008 |
| WO | WO 2011/096807 A1 * | 8/2011 |

OTHER PUBLICATIONS

French Search Report, dated May 6, 2013, French Application No. 1262234.

Bombardelli, Ezio, et al., "Passiflorine, A New Glycoside from Passiflora Edulis", *Phytochemistry*, vol. 14, (1975), 2661-2665.

Chassagne, David, et al., "A Cyanogenic Glycoside from Passiflora Edulis Fruits", *Phytochemistry*, vol. 49, No. 3, (1998), 757-759.

Dhawan, Kamaldeep, et al., "Passiflora: a review update", *Journal of Ethnopharmacology*, vol. 94, (2004), 1-23.

Sang, Shoko, et al., "Identification of the Strong Vasorelaxing Substance Scirpusin B, a Dimer of Piceatannal, from Passion Fruit (Passiflora edulis) Seeds", *Journal of Agricultural and Food Chemistry*, vol. 59, (2001), 6209-6213.

Seigler, David S., et al., "Cyanogenic allosides and glucosides from Passiflora edulis and Carica papaya", *Phytochemistry*, vol. 60, (2002), 873-882.

Zeraik, M.L., et al., "Quantification of isoorientin and total flavonoids in Passiflora edulis fruit pulp by HPLC-UV/DAD", *Microchemical Journal*, vol. 96, (2010), 86-91.

Han et al. "Development and Utilization of Resources of Passiflora Edulis." Food Science, 1985, pp. 1-6, with partial English translation. 8 pages.

Wang et al. "Recent Advances in the Study on Poly-and Oligo-Saccharides with Hypoglycemic Activity." Acta Pharmaceutica Sinica, vol. 39, pp. 1028-1033, with partial English translation. 8 pages.

International Preliminary Report on Patentability received for PCT Patent Application No. PCT/EP2013/077065, completed on Dec. 22, 2014, 16 pages (6 pages of English Translation and 10 pages of Original Document).

Ko et al., "Antioxidant activity of enzymatic extracts from Sargassum coreanum", Journal of the Korean Society of Food Science and Nutrition, vol. 39, No. 4, 2010, pp. 494-499 (English Abstract Submitted).

Matsui et al., "Extract of passion fruit (Passiflora edulis) seed containing high amounts of piceatannol inhibits melanogenesis and promotes collagen synthesis", Journal of agricultural and food chemistry, vol. 58, No. 20, 2010, pp. 11112-11118.

Office Action received for European Patent Application No. 13811898.9, dated Jul. 19, 2016, 5 pages of Original Document Only.

Office Action received for Korean Patent Application No. 10-2015-7018366, dated Nov. 29, 2019, 17 pages (8 pages of English Translation and 9 pages of Office Action).

* cited by examiner

EXTRACT OF PASSIONFLOWER SEEDS AND COSMETIC, PHARMACEUTICAL, DERMATOLOGICAL AND NUTRACEUTICAL COMPOSITIONS COMPRISING SAME

The invention relates to a composition comprising an extract of *Passiflora incarnata* or *Passiflora edulis* passionflower seeds, and preferentially *Passiflora edulis* seeds. The composition is advantageously cosmetic, pharmaceutical, dermatological or nutraceutical. Another subject matter of the invention is a process for extracting an extract of passionflower seeds and the extract able to be obtained by means of said process. The invention also relates to such a composition or such an extract for use in the prevention or treatment of disorders or pathological conditions of the skin, of the mucous membranes or of the skin appendages, for use in the prevention or treatment of vascular disorders, for use in combating oxidative stress, or for use in the prevention or treatment of adipose tissue modifications. Finally, the invention relates to a cosmetic care process for the skin, the skin appendages or the mucous membranes, with a view to improving the condition or appearance thereof, consisting in administering such a composition or such an extract.

Passionflowers

There about 500 species of passionflowers (*Passiflora*). The species are often distributed in warm, mild and tropical regions, particularly in the Americas, but are rather rare in Asia, Australia and tropical Africa.

Botany

Seedlings have the form of shrubs or climbing vines. The leaves are alternate, sometimes simple, lobed or palmate. The flowers, which may reach 9 cm in diameter, are bisexual or unisexual and regular. They are white and violet and have fine petaloid appendages covered with filiform appendages resembling Christ's crown of thorns. The fruit, 4 to 5 cm length, is egg-shaped and often yellow to orange in color. The most widespread species are notably *P. incarnata* and *P. edulis*.

Phytochemical Components

The most studied species are *P. incarnata* and *P. edulis*.

*P. incarnata*: the major components, represented by the flavonoid family, are present in large amounts in the leaves. It contains a high concentration of isovitexin. It also contains in small amounts simple indole alkaloids (harmane, harmine, etc.), sugars such as raffinose, sucrose, fructose and glucose, and essential oils and maltol, described as the molecule causing the sedative and anticonvulsant effects attributed to this plant.

*P. edulis*: a specific compound, passiflorine (cyclopropane triterpene glycoside), has been identified from a methanolic extract of dried leaves (E. Bombardelli et al., 1975). It contains isoorientin, a flavonoid not found in *P. incarnata*, and traces of essential oil and alkaloids identical to *P. incarnata*.

The fruit's flesh contains flavonoids, such as schaftoside, isoschaftoside, isoorientin, orientin, isovitexin and derivatives of luteolin (M. L. Zeraik, J. H. Yariwake-2010), and ascorbic acid (about 60 mg/100 g).

The flesh also contains glycosylated cyanogenic derivatives: prunasin, sambunigrin and amygdalin, and two recently-identified mandelonitrile-β-rutinosides (D. Chassagne and J. Crouzet, 1998; D. S. Seigler, 2002).

Toxicology

Cyanogenic components are present primarily in the aerial parts of various passionflower varieties.

Seed Characteristics

Seeds make up 6 to 12% of the *P. edulis* fruit and contain:

Polyphenols including piceatannol (structure similar to resveratrol) and its dimer scirpusin B (S. Sano; K. Sugiyama; T. Ito, 2011), substances with vasorelaxation and antioxidant effects.

Oil, 18% by solvent containing phytosterols (0.2% including campesterol, stigmasterol, sitosterol, avenasterol); 60% to 73% linoleic acid (omega 6), 14% to 20% oleic acid and 465 ppm tocopherols (G. Piobom, N. Barou et al., 2006; R. of V. V. Lopes et al.).

Sugars and Proteins

PRIOR ART

Use as Food

The fruit is believed to have been consumed since prehistoric times. In 16$^{th}$ century Peru the magnificent *Passiflora* flowers were already regarded as a remedy, and many passionflower species remain in use in many countries in common therapeutic practices.

Medical Use

Passionflowers (often the aerial parts and sometimes the fruits) are often used around the world as anxiolytics, sedatives, diuretics and analgesics (all the descriptions in "*Passiflora*: review update. K. Dhawan, S. Dhawan, A. Sharma, 2004"). Maltol and certain derivatives thereof are the source of this sedative effect.

This activity is more constant and more significant for *P. incarnata*.

Extracts of *P. incarnata* are able to reverse morphine dependence.

Anti-inflammatory effects have also been shown for extracts of *P. edulis* leaves.

The various polyphenol families are likely to contribute significantly to the antioxidant and anti-glycation effect of proteins (M. Rudnicki et al., 2007) of the aerial parts of *P. edulis*.

An anti-hypotensive effect of a methanolic extract of *P. edulis* fruit peels and a hypocholesterolemia effect of an extract of fiber-rich defatted seeds have also been shown.

A fruit decoction has an antitumor effect via inhibition of matrix metalloproteinases (MMP2 and MMP9) involved in tumor invasion, metastases and angiogenesis (S. S. Patel, 2009).

Use in Skincare Cosmetics

In Brazil *P. foetida* leaves are used cutaneously to treat inflammatory skin diseases. In Mauritius and Rodrigues decoctions of *P. suberosa* leaves are used in the bath to treat skin diseases.

DESCRIPTION OF THE INVENTION

The Applicant has discovered that extracts of passionflower seeds, particularly *Passiflora incarnata* or *Passiflora edulis* seeds, and even more advantageously *Passiflora edulis* seeds, have cosmetic and dermatological properties that have not been previously disclosed. Particularly, it is the first time that such extracts of passionflower seeds have been used as such, for their specific properties.

The subject matter of the invention is a composition comprising a peptide and sugar extract of passionflower seeds, particularly *Passiflora incarnata* or *Passiflora edulis* seeds, advantageously *Passiflora edulis* seeds, as an active agent and, if need be, a suitable excipient. The composition is advantageously cosmetic, pharmaceutical or dermatological. The composition may also be nutraceutical. Said composition is preferably formulated to be administered by external topically route or per os.

By "peptide and sugar extract" is meant an extract mainly or essentially comprising peptides and sugars. The proteins naturally present in the seeds have been hydrolyzed into peptides; advantageously the hydrolysis is enzymatic hydrolysis.

Within the context of the present invention, the peptide and sugar extract is advantageously obtained by enzymatic hydrolysis, more advantageously in the presence of at least one protease and at least one carbohydrase. More advantageously, it is able to be obtained by the process described further in the description.

In the peptide and sugar extract, the peptides advantageously have a molecular weight less than 3500 Da. These peptides encompass all the amino-acid based compounds present in the extract.

According to an advantageous variant of the invention, in the peptide and sugar extract, at least 90% of the peptides have a molecular weight less than 1200 Da.

In the peptide and sugar extract, advantageously at least 30% of the peptides, more advantageously at least 40% of the peptides, have a molecular weight less than 300 Da. According to an advantageous variant of the invention, between 30% and 50% of the peptides have a molecular weight less than 300 Da.

Advantageously according to the invention, between 30% and 70%, more advantageously between 40% and 60%, of the peptides of the extract have a molecular weight between 300 and 1200 daltons.

The molecular weight distribution of the peptides is expressed as a percentage in relation to the concentration of total peptides.

Typically, the peptide and sugar extract according to the invention does not substantially contain potentially-allergenic residual proteins.

The extract according to the present invention advantageously comprises 10% to 90% by weight peptides and 10% to 90% by weight total sugars, the percentages being expressed in relation to the total weight of said extract (before the optional addition of a drying support).

In the peptide and sugar extract, the weight ratio of peptides/sugars is advantageously greater than 0.75 and preferably between 1 and 2.

The peptide and sugar extract advantageously comprises 20% to 70%, advantageously 30% to 65%, typically 55%, by weight peptides, the percentages being expressed in relation to the total weight of said extract.

The peptide and sugar extract advantageously comprises 20% to 60%, advantageously 30% to 55%, typically 40%, by weight sugars, the percentages being expressed in relation to the total weight of said extract.

Particularly, the peptide and sugar extract advantageously comprises 20% to 70%, advantageously 30% to 65%, by weight peptides and 20% to 60%, advantageously 30% to 55%, by weight sugars, the percentages being expressed in relation to the total weight of said extract.

According to a preferred aspect of the invention, the peptide and sugar extract comprises 55% by weight peptides and 40% by weight sugars, the percentages being expressed in relation to the total weight of active material of said extract before the addition, for example, of an optional drying support. The remaining 5% are minerals (ashes) and other various molecules.

According to an advantageous variant of the invention, the composition contains 0.001% to 10%, typically 0.01% to 5%, by weight extract, expressed as a percentage of dry extract.

Another subject matter of the invention is a process for preparing a peptide and sugar extract of passionflower seeds, particularly *Passiflora incarnata* seeds or *Passiflora edulis* seeds, advantageously *Passiflora edulis* seeds, comprising at least one step of enzymatic hydrolysis under optimum pH and temperature conditions, known to the person skilled in the art. Enzymatic treatment of the dispersion may be followed, if need be, by heat treatment in order to denature the enzymes.

Advantageously according to the invention, the process for preparing a peptide and sugar extract of passionflower seeds comprises the following successive steps:
a) dispersion in an aqueous phase of grinded seeds, then
b) enzymatic treatment of the aqueous dispersion obtained in step a), then
c) if need be, heat treatment in order to denature the enzymes, and
d) collection of the peptide and sugar extract at the conclusion of step b) or c).

In step a), the aqueous phase is advantageously water.

The enzymatic treatment (step b)) is advantageously carried out by adding at least one protease and at least one carbohydrase, under optimum pH and temperature conditions, known to the person skilled in the art. For example, the pH is between 3.0 and 9.0. The temperature is typically between 20° C. and 90° C. In particular, the enzymatic treatment successively comprises a step b1) of adding a carbohydrase, advantageously selected from pectinases, cellulases, arabanases, hemicellulases, xylanases and β-glucanases, then a step b2) of adding an alkaline- or acid-type protease.

The hydrolysis step of the process according to the invention is very important, since it makes it possible to transform or "cut" into peptides the native proteins present in the passionflower seeds. This step also advantageously makes it possible to transform or "cut" into oligosaccharides or monosaccharides the polysaccharides present in the passionflower seeds.

In an advantageous variant of the process, the passionflower seeds are defatted prior to step a). Prior to being dispersed (step a)), the grinded seeds may be defatted, particularly in ethanol. Removing the lipids improves the subsequent filtration, ultrafiltration or nanofiltration steps. It is also and preferentially possible to use as the grinded seeds the oil cakes of these seeds, that is, the residue from preliminary oil extraction. This oil extraction may be carried out using solvent, using the supercritical $CO_2$ technique or, preferentially, by mechanical pressing.

During step d), the peptide and sugar extract is advantageously collected by extracting the dispersion obtained at the conclusion of step b), with shaking, advantageously at a pH between 3.0 and 9.0 and advantageously at a temperature between 20° C. and 90° C.

In an advantageous variant, the process comprises an additional step, between steps b), or if need be c), and d) of filtration or centrifugation, optionally followed by ultrafiltration, diafiltration or nanofiltration.

The filtration or centrifugation steps, particularly followed by membrane ultrafiltration or diafiltration, remove residual proteins. The nanofiltration steps remove mineral salts or free amino acids, for example.

The process according to the invention advantageously comprises a step of 15 kDa ultrafiltration, advantageously between 10 kDa and 15 kDa, which removes any potentially-allergenic residual proteins.

In a particular embodiment according to the invention, the process also comprises a nanofiltration step with, for example, a cut-off between 100 daltons and 300 daltons, advantageously between 130 daltons and 300 daltons, typically between 200 daltons and 300 daltons, in order to remove a portion of mineral salts or free amino acids or monosaccharides, following the ultrafiltration step.

Advantageously, the peptide and sugar extract may be stabilized by drying, by means of processes known to the person skilled in the art, in the presence or absence of a support of type maltodextrins or acacia fibers (Fibregum®, CNI), for example. The proportion of the support typically varies in a ratio from 0% to 80% by weight of the support in relation to the weight percent of the dry matter obtained in the liquid form of the extract. The extract is preferentially dried by freeze-drying in order to obtain a final powder. The final powder advantageously comprises 30% to 70% by weight dry matter of the extract, with the freeze-drying support bringing it up to 100%. More advantageously, the final powder comprises 50% by weight dry matter from the extract and 50% freeze-drying support.

Preferentially, as an example, the peptide and sugar extract may be obtained according to the following process:
a) preparation of a solution of an oil cake of passionflower seeds defatted by pressing, at a concentration of 10% dry matter in water;
b) enzymatic hydrolysis of carbohydrates by action of a cellulase (Cellulyve from Lyven, for example);
c) followed by hydrolysis by an acid protease (Prolyve PAC from Lyven, for example);
d) heat treatment in order to denature the enzymes;
e) centrifugation, ultrafiltration and diafiltration on 15 kDa membranes. This step particularly enables removal of potentially-allergenic residual proteins;
f) nanofiltration on a 200 Da membrane. This step particularly enables removal of mineral salts or free amino acids, for example.

Another subject matter of the present invention is an extract of passionflower seeds, particularly *Passiflora incarnata* or *Passiflora edulis* seeds, advantageously *Passiflora edulis* seeds, able to be obtained by the process mentioned above. Such an extract meets the specifications defined above. Particularly, such an extract advantageously contains 10% to 90% by weight peptides and 10% to 90% by weight sugars. More particularly, the extract comprises 20% to 70%, advantageously 30% to 65%, by weight peptides and 20% to 60%, advantageously 30% to 55%, by weight sugars.

The extract is advantageously used as an active agent in a composition such as a cosmetic, dermatological or pharmaceutical composition, which may comprise one or more suitable excipients. The composition may further comprise at least one other active compound in addition to passionflower hydrolysate. This other compound may be selected from all the compounds and functional equivalents thereof stated below:

This other compound may particularly be selected from active agents conventionally used in dermatology or cosmetics, such as emollients, moisturizing active agents, keratin-synthesis activators, keratoregulators, keratolytics, agents that restructure the cutaneous barrier (activators of synthesis of cutaneous lipids), peroxisome proliferator-activated receptor (PPAR) agonists, RXR or LXR agonists, sebum-regulating agents, anti-irritant agents, soothing agents, anti-inflammatory agents, antioxidants and anti-aging agents, depigmenting or hypodepigmenting agents, pigmenting agents, lipolytic agents or lipogenesis inhibitors or anti-cellulite or reducing agents, inorganic or organic sun filters and screens, antifungal compounds, preservatives, antibacterial agents, prebiotics and probiotics, antibiotics, immunomodulators.

More particularly, the agents for healing and/or restructuring the cutaneous barrier able to be used in combination are advantageously panthenol (vitamin B5), arabinogalactan, zinc oxide, ceramides, cholesterol, squalane and phospholipids.

The sebum-regulating agents able to be used in combination are advantageously selected from the group consisting of 5-alpha-reductase inhibitors. Zinc (and zinc derivatives such as the gluconate, salicylate and pyroglutamic acid salts thereof) and spironolactone also have sebum-suppressing activity. Other sebum-regulators of lipid origin acting on sebum quality, such as linoleic acid, are also of interest.

The anti-inflammatory and/or anti-irritant and/or soothing agent may be arabinogalactan.

The sunscreen active agents able to be used in combination are advantageously UVB and/or UVA sun filters and screens, such as inorganic and/or organic screens or filters known to the person skilled in the art who will adapt their selection and concentrations according to the required degree of protection.

The preservatives able to be used in combination are, for example, those generally used in cosmetics, molecules with antibacterial activity (pseudo-preservatives) such as caprylic derivatives, such as, for example, capryloyl glycine and glyceryl caprylate; hexanediol, sodium levulinate, and copper and zinc derivatives (gluconate and PCA).

This other compound may particularly be selected from plant extracts, particularly:
plant oils such as soybean oil and/or rapeseed oil, avocado oil (WO2004/012496, WO2004/012752, WO2004/016106, WO2007/057439), lupin oil and, advantageously, sweet white lupin oil (WO98/47479), or a mixture of these oils;
oleodistillate or concentrates of animal or plant oil, particularly of sunflower, more advantageously linoleic concentrates of sunflower, such as sunflower oil concentrated in unsaponifiables (Soline®-WO2001/21150), marketed by Laboratoires Expanscience, oils concentrated in unsaponifiables of type avocado oil, rapeseed oil, corn oil, useful particularly for their moisturizing and/or emollient, healing and/or cutaneous-barrier restructuring, anti-inflammatory and/or anti-irritant and/or soothing activity;
Unsaponifiables of plants or plant oil, advantageously avocado furans (Avocadofurane®), able to be obtained by the process described in international application WO 01/21605, avocado and/or soy unsaponifiables, more particularly a mixture of avocado furanic unsaponifiables and soy unsaponifiables, advantageously in a respective ratio of about ⅓-⅔ (such as Piascledine®), soy unsaponifiables (as obtained according to the process described in international application WO 01/51596), sterolic unsaponifiables (typically unsaponifiables whose content of sterols, methylsterols and triterpene alcohols is between 20% and 95% by weight, preferably 45-65% by weight, in relation to the total weight of unsaponifiable), phytosterols, esters of sterols and vitamin derivatives, useful particularly for their healing and/or cutaneous-barrier restructuring, anti-aging, anti-inflammatory activity;
Peptides or complexes of plant amino acids, particularly of avocado (such as those described in international application WO2005/105123), lupin peptides (such as those described in international application WO2005/102259), quinoa peptides (such as those described in international application WO2008/080974), maca peptides (such as those described in international application WO2004/112742), fermented or non-fermented soy peptides, rice peptides (such as those described in international application WO2008/009709), useful particularly for their moisturizing and/or emollient (avocado), keratoregulator (lupin, quinoa), healing and/or barrier restructuring (maca, quinoa, soy), anti-inflammatory and/or anti-irritant and/or soothing (lupin, quinoa), antioxidant (avocado), anti-aging (lupin, maca) or pigmenting (rice) activity, Schisandra peptides (such as those described in patent application FR 0955344), extract of Acacia macrostachya seeds (such as that described in patent application FR 0958525), extract of Vigna unguiculata seeds (such as that described in patent application FR 0958529);

Plant sugars, particularly avocado sugars (such as those described in application WO2005/115421), useful particularly for their keratoregulator, healing and/or cutaneous-barrier restructuring, anti-inflammatory and/or anti-irritant and/or soothing property;

Butyl avocadate (5 alpha Avocuta®), 5-alpha reductase inhibitor (WO 01/52837 and WO 02/06205) and typically regulator of increased seborrheic secretion seen in acne and dandruff;

Extracts rich in polyphenols, and more particularly extracts of avocado fruits (such as those described in application FR 1 061 055), extracts of maca leaves (such as those described in application FR 1 061 047), and extracts of the aerial parts of Gynandropsis gynandra (such as those described in application FR 1 061 051), Lupeol (FR 2 8 22 821, FR 2 857 596) useful particularly to promote healing;

Cupuaçu butter, particularly appreciated for its moisturizing properties.

This other compound may particularly be selected from oxazolines, particularly those selected from the group consisting of 2-undecyl-4-hydroxymethyl-4-methyl-1,3-oxazoline, 2-undecyl-4,4-dimethyl-1,3-oxazoline, (E)-4,4-dimethyl-2-heptadec-8-enyl-1,3-oxazoline, 4-hydroxymethyl-4-methyl-2-heptadecyl-1,3-oxazoline, (E)-4-hydroxymethyl-4-methyl-2-heptadec-8-enyl-1,3-oxazoline, 2-undecyl-4-ethyl-4-hydroxymethyl-1,3-oxazoline (preferably 2-undecyl-4,4-dimethyl-1,3-oxazoline, called OX-100 or Cycloceramide*; WO2004050052, WO2004050079, and WO2004112741). They are particularly useful for their anti-inflammatory and/or anti-irritant and/or soothing, antioxidant, depigmenting, immunomodulator activity.

All these combinations comprise at least one other active compound, in addition to extract of passionflower seeds, and may comprise two, three, four or more active compounds as described above.

The composition according to the invention may be formulated as various preparations suitable for topical application, oral, rectal, vaginal, nasal, auricular or bronchial administration, and parenteral administration.

According to a first variant, the various preparations are suitable for topical application and include particularly creams, emulsions, milks, ointments, lotions, oils, aqueous or water-alcohol or glycolic solutions, powders, patches, sprays, shampoos, varnishes or any other product for external application.

The composition comprising an extract of passionflower seeds having the indicated specifications is particularly intended for cosmetic, pharmaceutical, dermatological or nutraceutical use.

Within the context of cosmetic, pharmaceutical or dermatological use, the composition will advantageously be formulated as a preparation suitable for topical application. The composition comprising a peptide and sugar extract is particularly intended for cosmetic, pharmaceutical or dermatological use.

Within the context of use in food, for nutritive or cosmetic purposes ("cosmetic food"), the composition will advantageously be formulated as a preparation suitable for oral administration.

Another subject matter of the invention is the use of a peptide and sugar extract of passionflower seeds, having the specifications described above, for the manufacture of a cosmetic, pharmaceutical or dermatological composition, a nutraceutical composition or a functional food.

A functional food is a conventional food, or one which appears to be, which is part of a normal diet, and which has as a feature to provide beneficial physiological effects that exceed its usual nutritional functions or to reduce the risk of chronic diseases.

A subject matter of the invention is thus a functional food comprising the extract according to the invention.

Another subject matter of the invention is an extract according to the invention or a composition according to the invention for use to prevent and/or treat:
  disorders or pathological conditions of the skin and/or the mucous membranes and/or the skin appendages,
  vascular disorders,
  adipose tissue modifications,
  oxidative stress.

Particularly, the composition or extract according to the invention is intended for the prevention and/or treatment of allergic, inflammatory or irritative reactions or pathological conditions or disorders of the barrier or homeostasis of the skin, skin appendages (hair and nails) and/or immature, normal or mature/aged mucous membranes (gums, periodontium, genital mucosa).

Advantageously, the composition or extract according to the invention may be used for the prevention and/or treatment of reactions, disorders or pathological conditions of the:
  skin, such as acne, rosacea or erythrocouperosis, psoriasis, vascular disorders, diaper rash, atopic dermatitis, eczema, contact dermatitis, irritative dermatitis, allergic dermatitis, seborrheic dermatitis (cradle cap), psoriasis, sensitive skin, reactivate skin, dry skin (xerosis), dehydrated skin, skin with redness, cutaneous erythema, aged or photo-aged skin, photosensitive skin, pigmented skin (melasma, post-inflammatory pigmentation, etc.), depigmented skin (vitiligo), skin with cellulitis, loose skin, skin with stretch marks, scurf, chapping, insect bites, cracks particularly of the breasts, sunburns, inflammations due to rays of all kinds, irritations by chemical agents, physical agents (for example tension stress in expectant mothers), bacteriological agents, fungal or viral agents, parasitic agents (lice, mites, ringworm, acarina, dermatophytes), radiological agents or by innate immunity deficiencies (antimicrobial peptides) or acquired immunity deficiencies (cellular, humoral, cytokines), and/or
  mucous membranes such as gums and periodontium with gingivitis (sensitive gums in newborns, hygiene problems due to tobacco use, etc.), periodontal diseases, or genital mucosa with irritations of the male or female external or internal genital regions, and/or skin appendages such as immature, normal or mature nails (breakable, fragile nails, etc.) and hair (alopecia, dandruff, hirsutism, seborrheic dermatitidis, folliculitis), particularly scalp disorders such as androgenetic, acute, localized, cicatricial or congenital alopecia, alopecia in newborns, aerata, due to chemotherapy/radiotherapy or telogen effluvium, anagen effluvium, pilar dystrophy, trichotillomania, tinea or oily or dry dandruff.

The invention also relates to a cosmetic care process for the skin and/or skin appendages and/or mucous membranes, with a view to improving the condition and/or appearance thereof, consisting in administering a composition or extract according to the present invention.

Particularly, the cosmetic care process makes it possible to firm-up the skin and to decrease the "orange peel" effect advantageously by topical application on the skin and/or skin appendages and/or mucous membranes.

The invention relates to a cosmetic care process for the skin, with a view to preventing the aging thereof, consisting in applying on the skin a composition or extract according to the present invention.

The composition or extract according to the present invention may also be used advantageously in the prevention and/or treatment of vascular disorders, particularly redness and blotches.

The composition or extract according to the present invention may also be used advantageously in the prevention and/or treatment of adipose tissue modifications. Adipose tissue modifications are, in particular, cellulitis or the "orange peel" effect. The composition according to the invention makes it possible to firm-up the skin.

The modes of administration, dosing schedules and optimal pharmaceutical forms of the compounds and compositions according to the invention may be determined according to the criteria generally taken into account in the establishment of a pharmaceutical treatment, in particular a dermatological, cosmetic or veterinary treatment suitable for a patient or an animal, such as for example the age or the body weight of the patient or animal, the severity of the general condition of the patient or animal, tolerance to the treatment, noted side effects and skin type. Depending on the type of administration desired, the composition and/or the active compounds according to the invention may further include at least one pharmaceutically acceptable carrier, in particular a dermatologically acceptable carrier, or a cosmetically acceptable carrier. According to the first variant, a carrier suitable for external topical application is used. The composition according to the present invention may further include at least one pharmaceutical or cosmetic adjuvant known to the skilled person, selected from thickeners, preservatives, fragrances, colorants, chemical or inorganic filters, moisturizing agents, thermal spring waters, etc.

The following examples illustrate the invention.

Example 1

Extract According to the Invention

A peptide and sugar extract is obtained according to the following process:
a) preparation of a solution of oil cake of *Passiflora edulis* seeds defatted by pressing, at a concentration of 10% dry matter in water;
b) enzymatic hydrolysis of carbohydrates by action of a cellulase (Cellulyve, from Lyven);
c) followed by hydrolysis by an acid protease (Prolyve PAC, from Lyven);
d) heat treatment in order to denature the enzymes;
e) centrifugation, ultrafiltration and diafiltration on 15 kDa membranes in order to remove potentially-allergenic residual proteins;
f) nanofiltration on a 200 Da membrane in order to remove mineral salts or free amino acids or monosaccharides;
g) collection of the peptide and sugar extract.

The liquid peptide and sugar extract thus obtained has the following features:

1-Physicochemical Analysis (%/Total Dry Matter)
Dry extract (2 h, 105° C., ventilated oven): 9.7%
pH: 4.0
α-Amino nitrogen (OPA, leucine equivalent): 24%
Peptides (Kjeldahl, N×6.25): 56%
Soluble sugars (HPLC): 40% incl. glucose, fructose
Total ashes: 6%

2-Profile of Molecular Weight Distributions of the Peptides
Less than 130 Da: 26%
Between 130-300 Da: 17%
Between 300-1200 Da: 49%
Between 1200-3500 Da: 7%
Greater than 3500 Da: ≤1%

Example 2

Compositions for Topical Application

Several compositions for topical application are presented below. The peptide and sugar extract of passionflower seeds, example 1, may be incorporated into various cosmetic products, such as cleansers, oil-in-water emulsions, water-in-oil emulsions, oils, milks, lotions, shampoos, foaming products and sprays, the compositions of which are presented below as examples.

Moisturizing Cleanser

| Raw material/Trade name or INCI name | % |
| --- | --- |
| PURIFIED WATER | QS to 100% |
| BIOSACCHARIDE GUM | From 1 to 5% |
| BUTYLENE GLYCOL | From 1 to 5% |
| HYALURONIC ACID | From 0 to 5% |
| PEPTIDE AND SUGAR EXTRACT OF PASSIONFLOWER | From 0.001% to 10% |
| PRESERVATIVES | From 0 to 1% |
| CITRIC ACID MONOHYDRATE | From 0 to 1% |
| TROMETHAMINE | From 0 to 1% |

Cleanser for Sensitive Skin

| Raw material/Trade name or INCI name | % |
| --- | --- |
| CAPRYLOYL GLYCINE | From 0 to 1% |
| SODIUM HYDROXIDE | From 0 to 1% |
| SEQUESTRANT | From 0 to 1% |
| BUTYLENE GLYCOL | From 1 to 5% |
| BETA CAROTENE | From 0 to 2% |
| PEPTIDE AND SUGAR EXTRACT OF PASSIONFLOWER | From 0.001% to 10% |
| PRESERVATIVES | From 0 to 1% |
| PEG-32 | From 1 to 5% |
| PEG-7 PALMCOCOATE | From 1 to 5% |
| ZINC GLUCONATE | From 0 to 1% |
| CITRIC ACID | From 0 to 1% |
| PURIFIED WATER | QS to 100% |

-continued

| Raw material/Trade name or INCI name | % |
|---|---|
| FRAGRANCE | From 0 to 1% |
| POLOXAMER 184 | From 1 to 5% |

Anti-Aging Emulsion

| Raw material/Trade name or INCI name | % |
|---|---|
| LIQUID ISOPARAFFIN | From 5 to 20% |
| ISOCETYL STEARATE | From 5 to 20% |
| AL—MG HYDROXYSTEARATE | From 5 to 20% |
| ABIL WE 09 | From 1 to 5% |
| GLYCEROL | From 1 to 5% |
| MINERAL OIL | From 1 to 5% |
| MICRONIZED ZINC OXIDIZE | From 1 to 5% |
| BUTYLENE GLYCOL | From 1 to 5% |
| RETINOL | From 0 to 1% |
| VITAMIN C | From 0 to 5% |
| PEPTIDE AND SUGAR EXTRACT OF PASSIONFLOWER | From 0.01 to 10% |
| ISONONYL ISONONANOATE | From 1 to 5% |
| BEESWAX | From 1 to 5% |
| SODIUM TARTRATE | From 1 to 5% |
| SODIUM CHLORIDE | From 0 to 5% |
| GLYCINE | From 1 to 5% |
| PRESERVATIVES | From 0 to 1% |
| CHOLESTEROL | From 0 to 1% |
| PHYTOSPHINGOSINE | From 0 to 1% |
| TARTARIC ACID | From 0 to 1% |
| PURIFIED WATER | QS to 100% |

Restructuring Emulsion

| Raw material/Trade name or INCI name | % |
|---|---|
| HYDROGENATED POLYDECENE | From 5 to 20% |
| LAURYLGLUCOSIDE-GLYSTEARATE | From 1 to 5% |
| DICAPRYLYL CARBONATE | From 1 to 5% |
| GLYCEROL | From 5 to 20% |
| CARBOPOL | From 0 to 1% |
| XANTHAN GUM | From 0 to 1% |
| ASIATIC ACID | From 0 to 1% |
| VITAMIN B5 | From 0 to 5% |
| PEPTIDE AND SUGAR EXTRACT OF PASSIONFLOWER | From 0.01 to 10% |
| SODIUM HYDROXIDE | From 0 to 1% |
| PRESERVATIVES | From 0 to 1% |
| CITRIC ACID | From 0 to 1% |
| PURIFIED WATER | QS to 100% |

Slimming Oil

| Raw material/Trade name or INCI name | % |
|---|---|
| SOLUBILIZER | From 0 to 1% |
| SWEET ALMOND OIL | From 5 to 20% |
| COPRA CAPRYLATE/CAPRATE | QS to 100% |
| REFINED MACADAMIA | From 5 to 20% |
| GLYCEROL CAPRYLOCAPRATE | From 5 to 20% |
| NAT ALPHA BISABOLOL | From 0 to 1% |
| ALPHA TOCOPHEROL | From 0 to 1% |
| EXTRACT OF IVY | From 0 to 5% |
| PEPTIDE AND SUGAR EXTRACT OF PASSIONFLOWER | From 0.01 to 10% |
| PRESERVATIVE | From 0 to 1% |
| ESTER | From 0 to 1% |

Milk for Dry, Atopic Skin

| Raw material/Trade name or INCI name | % |
|---|---|
| SWEET ALMOND OIL | From 1 to 5% |
| CORN OIL | From 1 to 5% |
| STEARIC ACID | From 1 to 5% |
| C16 C18 CETYL ALCOHOL | From 0 to 1% |
| ANTIFOAM 70414 | From 0 to 1% |
| LAURIC ALCOHOL 11OE | From 1 to 5% |
| PEG 300 MONOLAURATE | From 0 to 1% |
| GLYCEROL MONOLEATE | From 0 to 1% |
| GLYCEROL MONOSTEARATE | From 1 to 5% |
| VITAMIN B12 | From 0 to 5% |
| PEPTIDE AND SUGAR EXTRACT OF PASSIONFLOWER | From 0.1 to 10% |
| PRESERVATIVES | From 0 to 1% |
| CITRIC ACID | From 0 to 1% |
| TRISODIUM CITRATE | From 0 to 1% |
| PURIFIED WATER | QS to 100% |
| FRAGRANCE | From 0 to 1% |
| PEANUT OIL | From 1 to 5% |
| HYDROGENATED PALM OIL | From 1 to 5% |

Foam

| Raw material/Trade name or INCI name | % |
|---|---|
| PURIFIED WATER | QS to 100% |
| LAUROAMPHOACETATE | From 5 to 20% |
| COCOGLUCOSIDE | From 5 to 20% |
| SURFACTANT 1 | From 5 to 20% |
| SURFACTANT 2 | From 5 to 20% |
| PEG 6000 DISTEARATE | From 1 to 5% |
| PRESERVATIVES | From 1 to 5% |
| PEPTIDE AND SUGAR EXTRACT OF PASSIONFLOWER | From 0.001% to 10% |
| CHAMOMILE EXTRACT | From 1 to 5% |
| CITRIC ACID MONOHYDRATE | From 0 to 1% |
| SEQUESTRANT | From 0 to 1% |
| FRAGRANCE | From 0 to 1% |
| SODIUM HYDROXIDE | From 0 to 1% |

Soothing Spray

| Raw material/Trade name or INCI name | % |
|---|---|
| PURIFIED WATER | QS to 100% |
| TRILAURETH-4 PHOSPHATE | From 1 to 5% |
| DICAPRYLYL CARBONATE | From 1 to 5% |
| BUTYLENE GLYCOL | From 1 to 5% |
| ERYTHRITYL ESTER | From 1 to 5% |
| LIQUID MINERAL OIL | From 1 to 5% |
| SHEA BUTTER | From 0 to 1% |
| VEGETABLE OIL | From 0 to 1% |
| PRESERVATIVES | From 0 to 1% |
| LYCOPENE | From 0 to 5% |
| PEPTIDE AND SUGAR EXTRACT OF PASSIONFLOWER | From 0.01 to 10% |
| SODIUM HYDROXIDE | From 0 to 1% |
| FRAGRANCE | From 0 to 1% |
| XANTHAN GUM | From 0 to 1% |
| CARBOPOL | From 0 to 1% |
| SEQUESTRANT | From 0 to 1% |
| CITRIC ACID | From 0 to 1% |

Purifying Cleansing Cream

| Raw material/Trade name or INCI name | % |
|---|---|
| PURIFIED WATER | QS to 100% |
| ARLATONE | From 10 to 30% |
| COCOGLUCOSIDE | From 5 to 20% |

-continued

| Raw material/Trade name or INCI name | % |
|---|---|
| HYDROXYPROPYL GUAR | From 1 to 5% |
| CAPRYLOYL GLYCINE | From 0 to 2% |
| PRESERVATIVES | From 0 to 2% |
| FRAGRANCE | From 0 to 1% |
| CITRIC ACID | From 0 to 1% |
| ZINC PCA | From 0 to 1% |
| PEPTIDE AND SUGAR EXTRACT OF PASSIONFLOWER | From 0.001% to 10% |

Anti-Acne Emulsion

| Raw material/Trade name or INCI name | % |
|---|---|
| PEG 40 STEARATE | From 1 to 5% |
| PEG 5 GLYCERYL STEARATE | From 1 to 5% |
| CERESIN WAX | From 1 to 5% |
| GLYCEROL MONOSTEARATE | From 1 to 5% |
| SORBITAN STEARATE | From 0 to 2% |
| CETYL ALCOHOL | From 0 to 2% |
| DI-MALATE ALCOHOL | From 5 to 20% |
| VITAMIN E | From 0 to 1% |
| VITAMIN B3 | From 0 to 5% |
| LINOLEIC ACID | From 0 to 1% |
| PEPTIDE AND SUGAR EXTRACT OF PASSIONFLOWER | From 0.01 to 10% |
| BUTYLENE GLYCOL | From 1 to 5% |
| PIROCTOLAMINE | From 0 to 1% |
| PRESERVATIVES | From 0 to 1% |
| GLYCEROL | From 1 to 10% |
| XANTHAN GUM | From 0 to 1% |
| ZINC PCA | From 0 to 2% |
| RICE STARCH | From 1 to 5% |
| NYLON 6 | From 0 to 2% |
| POLYACRYLAMIDE GEL | From 1 to 5% |
| VITAMIN B6 | From 0 to 1% |
| FRAGRANCE | From 0 to 1% |
| PURIFIED WATER | QS to 100% |

Anti-Redness Emulsion

| Raw material/Trade name or INCI name | % |
|---|---|
| PEG 40 STEARATE | From 1 to 5% |
| PEG 5 GLYCERYL STEARATE | From 1 to 5% |
| CERESIN WAX | From 1 to 5% |
| GLYCEROL MONOSTEARATE | From 1 to 5% |
| SORBITAN STEARATE | From 0 to 2% |
| CETYL ALCOHOL | From 0 to 2% |
| DI-MALATE ALCOHOL | From 5 to 20% |
| ESCULOSIDE | From 0 to 2% |
| SOPHORA JAPONICA | From 0 to 5% |
| VITAMIN E | From 0 to 1% |
| PEPTIDE AND SUGAR EXTRACT OF PASSIONFLOWER | From 0.01 to 10% |
| BUTYLENE GLYCOL | From 1 to 5% |
| PIROCTOLAMINE | From 0 to 1% |
| PRESERVATIVES | From 0 to 1% |
| GLYCEROL | From 1 to 10% |
| XANTHAN GUM | From 0 to 1% |
| ZINC PCA | From 0 to 2% |
| RICE STARCH | From 1 to 5% |
| NYLON 6 | From 0 to 2% |
| POLYACRYLAMIDE GEL | From 1 to 5% |
| VITAMIN B6 | From 0 to 1% |
| FRAGRANCE | From 0 to 1% |
| PURIFIED WATER | QS to 100% |

Reparative Care

| Raw material/Trade name or INCI name | % |
|---|---|
| PEG 40 STEARATE | From 1 to 5% |
| PEG 5 GLYCERYL STEARATE | From 1 to 5% |
| CERESIN WAX | From 1 to 5% |
| GLYCEROL MONOSTEARATE | From 1 to 5% |
| SORBITAN STEARATE | From 0 to 2% |
| CETYL ALCOHOL | From 0 to 2% |
| DI-MALATE ALCOHOL | From 5 to 20% |
| VITAMIN E | From 0 to 1% |
| COENZYME Q10 | From 0 to 2% |
| CERAMIDE | From 0 to 5% |
| PEPTIDE AND SUGAR EXTRACT OF PASSIONFLOWER | From 0.01 to 10% |
| BUTYLENE GLYCOL | From 1 to 5% |
| PIROCTOLAMINE | From 0 to 1% |
| PRESERVATIVES | From 0 to 1% |
| GLYCEROL | From 1 to 10% |
| XANTHAN GUM | From 0 to 1% |
| ZINC PCA | From 0 to 2% |
| RICE STARCH | From 1 to 5% |
| NYLON 6 | From 0 to 2% |
| POLYACRYLAMIDE GEL | From 1 to 5% |
| VITAMIN B6 | From 0 to 1% |
| FRAGRANCE | From 0 to 1% |
| PURIFIED WATER | QS to 100% |

Depigmenting Emulsion

| Raw material/Trade name or INCI name | % |
|---|---|
| ISONONYL ISONONANOATE | From 1 to 10% |
| ISOCETYL STEARATE | From 1 to 10% |
| PEG 40 STEARATE | From 1 to 5% |
| PEG 5 GLYCERYL STEARATE | From 1 to 5% |
| PRESERVATIVES | From 0 to 1% |
| C16 C18 CETYL ALCOHOL | From 0 to 2% |
| PPG/SMDI POLYMER | From 0 to 1% |
| SALICYLIC ACID | From 0 to 2% |
| SQUALANE GEL | From 0 to 2% |
| DIOCTYL ETHER | From 1 to 10% |
| DI-MALATE ALCOHOL | From 1 to 10% |
| SUNFLOWER EXTRACT | From 1 to 10% |
| TROMETHAMINE | From 1 to 5% |
| BUTYLENE GLYCOL | From 1 to 10% |
| TRISODIUM CITRATE | From 0 to 1% |
| SCLEROTIUM GUM | From 0 to 1% |
| RICE STARCH | From 1 to 10% |
| POLYACRYLAMIDE GEL | From 0 to 1% |
| VITAMIN C | From 0 to 2% |
| GLYCINE | From 0 to 2% |
| FRAGRANCE | From 0 to 1% |
| VITAMIN E | From 0 to 2% |
| CITRIC ACID | From 0 to 1% |
| SEPIWHITE | From 0 to 2% |
| PEPTIDE AND SUGAR EXTRACT OF PASSIONFLOWER | From 0.01 to 10% |
| PURIFIED WATER | QS to 100% |

Antibacterial Stick Roll-on

| Raw material/Trade name or INCI name | % |
|---|---|
| PURIFIED WATER | QS to 100% |
| BUTYLENE GLYCOL | From 1 to 5% |
| BENZOYL PEROXIDE | From 0 to 2% |
| CAPRYLOYL GLYCINE | From 0 to 5% |
| ZINC PCA | From 0 to 5% |
| PEPTIDE AND SUGAR EXTRACT OF PASSIONFLOWER | From 0.1 to 10% |
| CARBOMER | From 0 to 2% |
| PRESERVATIVES | From 0 to 1% |

Scrub

| Raw material/Trade name or INCI name | % |
|---|---|
| CITRIC ACID | From 0 to 1% |
| TROMETHAMINE | From 0 to 1% |

Scrub

| Raw material/Trade name or INCI name | % |
|---|---|
| ARLATONE DUO | From 5 to 20% |
| EXFOLIATING AGENT | From 1 to 10% |
| SCLEROTIUM GUM | From 1 to 10% |
| PRESERVATIVES | From 0 to 1% |
| CAPRYLOYL GLYCINE | From 0 to 1% |
| SODA | From 0 to 1% |
| PEPTIDE AND SUGAR EXTRACT OF PASSIONFLOWER | From 0.01 to 10% |
| SEQUESTRANT | From 0 to 1% |
| CITRIC ACID | From 0 to 1% |
| PURIFIED WATER | QS to 100% |
| FRAGRANCE | From 0 to 1% |

Keratinizing Fluid

| Raw material/Trade name or INCI name | % |
|---|---|
| CETYL ALCOHOL | From 1 to 5% |
| SILICONE 345 | From 1 to 5% |
| ANTIOXIDANT | From 0 to 1% |
| PURIFIED WATER | QS to 100% |
| CETRIMONIUM CHLORIDE | From 0 to 5% |
| QUININE | From 0 to 5% |
| VITAMIN B5 | From 0 to 5% |
| PEPTIDE AND SUGAR EXTRACT OF PASSIONFLOWER | From 0.01 to 10% |
| HYDROLYZED WHEAT PROTEIN | From 0 to 1% |
| PRESERVATIVE | From 0 to 2% |
| FRAGRANCE | From 0 to 1% |
| pH ADJUSTER | From 0 to 1% |

Antidandruff Shampoo

| Raw material/Trade name or INCI name | % |
|---|---|
| PURIFIED | QS to 100% |
| LAUROAMPHOACETATE | From 5 to 20% |
| COCOGLUCOSIDE | From 5 to 20% |
| PEG 6000 DISTEARATE | From 1 to 5% |
| PRESERVATIVES | From 0 to 2% |
| VITAMIN F | From 0 to 5% |
| PIROCTONE OLAMINE | From 0 to 2% |
| PEPTIDE AND SUGAR EXTRACT OF PASSIONFLOWER | From 0.01 to 10% |
| ZINC PYRITHIONE | From 0 to 1% |
| pH ADJUSTER | From 0 to 1% |
| SEQUESTRANT | From 0 to 1% |
| FRAGRANCE | From 0 to 1% |

Detangling Fluid

| Raw material/Trade name or INCI name | % |
|---|---|
| CETEARYL ALCOHOL CETEARETH-33 | From 1 to 5% |
| QUATERNIUM-82 | From 0 to 2% |
| PURIFIED WATER | QS to 100% |
| HYDROLYZED WHEAT PROTEIN | From 0 to 5% |
| PRESERVATIVES | From 0 to 2% |
| pH ADJUSTER | From 0 to 1% |
| FRAGRANCE | From 0 to 1% |

| Raw material/Trade name or INCI name | % |
|---|---|
| CYSTEINE | From 0 to 5% |
| PEPTIDE AND SUGAR EXTRACT OF PASSIONFLOWER | From 0.01 to 10% |

Fortifying Capillary Lotion

| Raw material/Trade name or INCI name | % |
|---|---|
| PURIFIED WATER | QS to 100% |
| METHYL PROPANEDIOL | From 5 to 20% |
| PRESERVATIVE | From 0 to 2% |
| pH ADJUSTER | From 0 to 1% |
| FRAGRANCE | From 0 to 1% |
| BIOTIN | From 0 to 5% |
| VITAMIN B9 | From 0 to 5% |
| PEPTIDE AND SUGAR EXTRACT OF PASSIONFLOWER | From 0.01 to 10% |
| BETA-SITOSTEROL | From 0 to 1% |
| ETHYLHEXYL COCOATE | From 0 to 5% |
| PEG-40 CASTOR OIL | From 0 to 5% |

Photoprotecting Stick

| Raw material/Trade name or INCI name | % |
|---|---|
| CASTOR OIL | QS to 100% |
| OLEIC ALCOHOL | From 10 to 20% |
| PALM OIL | From 10 to 20% |
| POLYGLYCERIN-3-BEESWAX | From 10 to 20% |
| CANDELILLA WAX | From 10 to 20% |
| HECTORITE | From 10 to 20% |
| TITANIUM DIOXIDE | From 0 to 5% |
| PEPTIDE AND SUGAR EXTRACT OF PASSIONFLOWER | From 0.01 to 10% |
| SHEA BUTTER | From 0 to 5% |
| VITAMIN E | From 0 to 1% |

SPF 50+ Sun Cream

| Raw material/Trade name or INCI name | % |
|---|---|
| B4 PURIFIED WATER | QS to 100% |
| TITANIUM OXIDE | From 10 to 20% |
| CYCLOPENTASILOXANE | From 5 to 15% |
| OCTYL PALMITATE | From 5 to 15% |
| C12-C15 ALKYL BENZOATE | From 5 to 10% |
| DECYL PENTANOATE | From 5 to 10% |
| ZINC OXIDE | From 5 to 10% |
| GLYCEROL | From 1 to 5% |
| PEG-45/DODECYL GLYCOL COPOLYMER | From 1 to 5% |
| PEPTIDE AND SUGAR EXTRACT OF PASSIONFLOWER | From 0.01 to 10% |
| SODIUM CHLORIDE | From 1 to 5% |
| DEXTRIN PALMITATE | From 1 to 2% |
| VITAMIN E | From 0 to 2% |
| PRESERVATIVES | From 0 to 2% |
| HYDROXYPROPYL GUAR | From 0 to 1% |
| *ALOE VERA* | From 0 to 1% |
| SODIUM HYDROXIDE | From 0 to 1% |
| EDTA 2 Na | From 0 to 1% |
| ZINC GLUCONATE | From 0 to 1% |

SPF 50+ Sun Spray

| Raw material/Trade name or INCI name | % |
|---|---|
| GLYCEROL CAPRYLOCAPRATE | From 5 to 20% |
| CYCLOPENTASILOXANE | From 10 to 20% |

-continued

| Raw material/Trade name or INCI name | % |
|---|---|
| DICAPRYLYL CARBONATE | From 5 to 20% |
| TINOSORB S | From 1 to 10% |
| TITANIUM OXIDE 100 | From 10 to 20% |
| HECTORITE | From 0 to 5% |
| ALPHA TOCOPHEROL | From 0 to 2% |
| LAURYLGLUCOSIDE-GLYSTEARATE | From 0 to 10% |
| B4 PURIFIED WATER | QS to 100% |
| CITRIC ACID | From 0 to 2% |
| PENTYLENE GLYCOL | From 0 to 5% |
| GLYCEROL | From 0 to 5% |
| XANTHAN GUM | From 0 to 2% |
| PEPTIDE AND SUGAR EXTRACT OF PASSIONFLOWER | From 0.01 to 10% |
| ALOE VERA | From 0 to 1% |
| ZINC GLUCONATE | From 0 to 1% |
| PRESERVATIVES | From 0 to 2% |
| TINOSORB M | From 1 to 10% |

Varnish for Fragile and Breakable Fingernails

| Raw material/Trade name or INCI name | % |
|---|---|
| ACRYLATE COPOLYMER | From 15 to 30% |
| ETHANOL | QS to 100% |
| ACETONE | From 5 to 20% |
| PEPTIDE AND SUGAR EXTRACT OF PASSIONFLOWER | From 0.01% to 5% |

Example 3

Compositions for Oral Administration

Extracts of *Passiflora edulis* may be advantageously integrated into oral compositions, typically in compositions allowing the administration of 50 mg to 200 mg of extract of *Passiflora edulis* per day.

1/Anti-Stretch Marks Composition in the Form of Soft Capsules

| | |
|---|---|
| EXTRACT of *Passiflora edulis* | 30 mg |
| Awara oil | 60 mg |
| Unsaponifiable-rich rapeseed oil | 300 mg |
| Group B vitamin (B1, B2, B3, B5, B6, B9, B12) | QS to 100% RDA |
| Tocotrienols | QS to 50% RDA |
| Vitamin E | |
| Beeswax | |
| Soy lecithin | |
| Alimentary gelatin | |
| Glycerin | QS to 1 soft capsule |

This composition is administered as four to six 500 mg capsules per day.

2/Anti-Hair Loss Tablets

| | |
|---|---|
| EXTRACT of *Passiflora edulis* | 25 mg |
| Extracts of cereals (corn, buckwheat, millet, spelt) rich in sulfur amino acids | 200 mg |
| Vitamin C | QS to 50% RDA |
| Fish cartilage glycosaminoglycans | 200 mg |
| Glucidex IT 19 (compression agent) | QS to one 800 mg tablet |

This composition is administered as five to eight tablets per day.

3/Examples of Slimming Powder Sticks

| | |
|---|---|
| EXTRACT of *Passiflora edulis* | 100 mg |
| Polyphenol-rich tea extract | 100 mg |
| OPC-rich grape extract | 50 mg |
| Plant beta-glucans | 100 mg |
| Xanthan gum | 1 mg |
| Sodium ascorbate | 0.3 mg |
| Maltodextrin | QS to 5 g |

This composition is administered twice per day.

| | |
|---|---|
| EXTRACT of *Passiflora edulis* | 100 mg |
| Extract of *Centella asiatica* | 100 mg |
| Magnesium, selenium, manganese | QS to 100% RDA |
| Xanthan gum | 1 mg |
| Sodium ascorbate | 0.3 mg |
| Maltodextrin | QS to 5 g |

This composition is administered twice per day.

4/Example of Chocolate-Flavored Cereal Bar

| | |
|---|---|
| EXTRACT of *Passiflora edulis* | 200 mg |
| Lycopene | 6 mg |
| Astaxanthin | 4 mg |
| Fucoxanthin | 4 mg |
| Lutein in microencapsulated form | 4 mg |
| Microencapsulated tocotrienol | QS to 100% RDA vitamin E |
| Dark chocolate, oligofructose, sugar, fructose syrup, fat-reduced cocoa powder, crunchy cereals, powdered skim milk, almonds, glycerol, sorbitol, vegetable oils, glucose syrup, flavoring, sweetened condensed milk, soy lecithin, fatty acid mono-and diglycerides, caramelized syrup, maltodextrin, salt, potassium sorbate, alpha tocopherol. | QS to 50 g bar |

This composition is administered once per day.

5/Example of Vanilla-Flavored Cereal Bar

| | |
|---|---|
| EXTRACT of *Passiflora edulis* | 200 mg |
| Extracts of cereals (corn, buckwheat, millet, spelt) rich in sulfur amino acids | 200 mg |
| Fish cartilage glycosaminoglycans | 200 mg |
| Polyphenol-rich extract of green tea | 200 mg |
| Oligofructose, sugar, fructose syrup, crunchy cereals, powdered skim milk, almonds, glycerol, sorbitol, vegetable oils, glucose syrup, flavoring, sweetened condensed milk, soy lecithin, fatty acid mono-and diglycerides, caramelized syrup, maltodextrin, salt, potassium sorbate, alpha tocopherol. | QS to 50 g bar |

This composition is administered once per day.

6/Example of a Praline-Flavored Milk Beverage

| | |
|---|---|
| EXTRACT of *Passiflora edulis* | 200 mg |
| Polyphenol-rich extract of green tea | 100 mg |
| Group B vitamin (B1, B2, B3, B5, B6, B9, B12) | QS to 100% RDA |
| Zn, Mg, Se | QS to 100% RDA |
| Skimmed milk powder, flavoring, fructose, egg white, hazel nuts, sugar, caramel, beta-carotene, xanthan gum, aspartame, potassium acesulfame, soy lecithin, maltodextrin | QS to one 30 g packet |

This composition is administered once per day.

Example 4

Tests of Biological Activities of the Extract According to the Invention

The peptide and sugar extract of passionflower of example 1 is referred to as passionflower hydrolysate in the example below.

A-Screening of Activities on Normal Human Keratinocytes (NHK)

The biological activities of passionflower hydrolysate were evaluated by a test of the modulation of gene expression on NHK cultures: expression profile study on Agilent Whole Genome Microarray chips comprising 43,376 gene sequences.

a-Materials and Methods

NHK were cultivated for 24 hours and then treated with passionflower hydrolysate at a concentration of 0.05% dry matter. Keratinocytes were treated in a staggered manner (72 h, 24 h, 6 h) such that each analysis point is cultured for the same duration, 72+24 hours.

Expression of the selected genes was evaluated by quantitative RT-PCR.

The intensity ratios ($R_i$) of the treated samples versus the control were calculated for each gene and each treatment condition.

b-Results

The results deemed significant are those for which $R_i$ is >2 for each kinetics time but also at two consecutive times, either 3-6 h or 6-24 h.

The following was shown:

An anti-apoptotic effect, expressed by inhibition by passionflower hydrolysate of transcription factor ATF3, itself a transcription factor of pro-apoptotic genes of the GADD family, and other stress-inducible pro-apoptotic genes such as DDIT4, FANCE, IRS2 and its target FOXO3.

An activator effect on cell proliferation, via induction of genes of cyclins CCNB1, CCND1 and cyclin-dependent kinase CDK1. This observation is supported by the induction of genes involved in various cell activation-related mechanisms such as DNA replication (RFC4, TIPIN), mitosis (CDCA7, CDCA8), splicing (SF3A3, SRSF7), RNA transcription (POP1) and protein translation (WDR3, NOP56, MRTO4).

An activator effect on sterol biosynthesis, suggesting a protective activity on the stratum corneum and thus on the epidermal barrier. That occurs by means of activation of the following genes: ACAT1, ACAT2, HMGCS1, HMGCR, MVD, FDPS, FDFT1, SQLE, LSS, MSMO1/SC4MOL, DHCR, EBP, DHCR7, LIPA and SOAT1.

An activator effect on antioxidant mechanisms, which occurs by induction of metallothioneins MT1A, MT1B, MT1E, MT1F, MT1G, MT1H, MT1L, MT1M, MT1X, MT2A, stimulation of genes of several enzymes involved in biosynthesis of glutathione: GSTA4, GSTM3, MGST2, GPX1, GPX2, GPX8, GSS, PRDX1 or of superoxide dismutase SOD1 and stimulation of genes of several transcription factors encoded by MAFB, ATF3 and JUN, factors important for the oxidative stress response by means of their binding to antioxidant response element (ARE) and hypoxia response element (HRE) motifs.

B-Screening of Activities on Normal Human Fibroblasts (NHF)

The biological activities of passionflower hydrolysate were evaluated by a test of the modulation of gene expression on NHF cultures. Thus, expression of 46 genes involved in the biology of the dermis, the restructuring of connective tissues and ageing, and 46 genes involved in key functions of the epidermis, such as the barrier function, in direct relation to skin hydration, antioxidant response, or pigmentation by melanocytes, in the presence of passionflower hydrolysate in the culture medium, were studied by qRT-PCR.

a-Materials and Methods

Passionflower hydrolysate was diluted in culture medium. NHF cultures are treated with 0.01% and 0.05% passionflower hydrolysate for 24 hours (and with the control molecule, TGFβ1). At the conclusion of the application, the differences in gene expression were analyzed by qRT-PCR. Changes in gene expression induced by passionflower hydrolysate are expressed as relative quantity (RQ) in relation to the condition corresponding to an untreated culture (if RQ>1: stimulation of gene expression, and RQ<1: inhibition of gene expression).

b-Results

Activator Effect on Antioxidant Mechanisms

The 0.01% passionflower hydrolysate induces expression of the gene for MSRA (mitochondrial peptide methionine sulfoxide reductase A), a mitochondrial enzyme known for its antioxidant power.

Similarly, the 0.05% passionflower hydrolysate induces expression of the gene for NQO1 (NAD(H)dehydrogenase quinone 1), an antioxidant enzyme with activity identical to superoxide dismutase.

By increasing MSQRA and NQO1, passionflower hydrolysate enables fibroblasts of the human dermis to be more resistant to the oxidative damage responsible for cell aging and, therefore, skin aging.

Effect on Compounds of the Extracellular Matrix

The 0.01% and 0.05% passionflower hydrolysates induce expression of the SDC1 gene encoding syndecan 1, which is a transmembrane proteoglycan playing a crucial role in tissue cohesion.

TABLE 1

| Tests | Gene name | 0.01% passionflower hydrolysate | | 0.05% passionflower hydrolysate | |
|---|---|---|---|---|---|
| | | RQ | p-value | RQ | p-value |
| MSRA-Hs00737165_m1 | Mitochondrial peptide methionine sulfoxide reductase A | 1.8542 | 0.0465 | | |
| SDC$_1$-Hs00896424_g1 | Syndecan-1 | 1.5042 | 0.0491 | 1.5667 | 0.0388 |
| NQO$_1$-Hs00168547_m1 | NAD(H)dehydrogenase, quinone 1 | | | 2.0835 | 0.0414 |

C-Screening of Activities on Melanized Reconstructed Skin

The biological activities of passionflower hydrolysate were evaluated by a test of modulation of gene expression on melanized reconstructed skin. Thus, expression of 46 genes involved in the biology of the dermis, the restructuring of connective tissues and ageing, and 46 genes involved in key functions of the epidermis, such as the barrier function, in direct relation to skin hydration, antioxidant response, or pigmentation by melanocytes, in the presence of passionflower hydrolysate in the culture medium, were studied by qRT-PCR.

a-Materials and Methods

Passionflower hydrolysate was diluted in the culture medium. Skin samples are treated with 0.01% and 0.05% passionflower hydrolysate for 24 hours (and with the control molecule, TGFβ1). At the conclusion of the application, the differences in gene expression were analyzed by qRT-PCR. Changes in gene expression induced by passionflower hydrolysate are expressed as relative quantity (RQ) in relation to the condition corresponding to an untreated culture (if RQ>1: stimulation of gene expression, and RQ<1: inhibition of gene expression).

b-Results

Effect on Genes Involved in Dermal/Epidermal Cohesion

The 0.05% passionflower hydrolysate induces expression of LAMC2, the gene encoding laminin C2; passionflower hydrolysate can thus help strengthen the dermo-epidermal junction and therefore promote firmness of the skin.

Effect on Genes Involved in the Barrier Function of the Skin

The 0.05% passionflower hydrolysate induces expression of the gene encoding involucrin (IVL), a structural protein of the corneal envelope involved in corneocyte initiation and maturation that therefore plays an essential role in the barrier function of the skin. It also stimulates expression of the gene for filaggrin (FLG), also involved in hydration and the barrier function.

Effect on Other Genes

Passionflower hydrolysate decreases expression of MC1R, involved in the melanogenesis process, PTGS2, involved in the inflammatory response, and BIRC5, anti-apoptotic factor and stem cell marker.

TABLE 2

| Tests | Gene name | 0.01% passionflower hydrolysate RQ | 0.01% passionflower hydrolysate p-value | 0.05% passionflower hydrolysate RQ | 0.05% passionflower hydrolysate p-value |
|---|---|---|---|---|---|
| LACMC2-Hs01043711_m1 | Laminin subunit gamma-2 | | | 2.7769 | 0.026 |
| IVL-Hs00846307_s1 | Involucrin | | | 1.4151 | 0.0048 |
| MC1R-Hs00267167_s1 | Melanocyte-stimulating hormone receptor | | | 0.7131 | 0.0194 |
| PTGS2-Hs01573476_g1 | Prostaglandin G/H synthase 2 | | | 0.5185 | 0.0438 |
| BIRC5-Hs00977611_g1 | Baculoviral IAP repeat-containing protein 5 (survivin) | | | 0.5122 | 0.0007 |
| NTRK2-Hs01093103_m1 | BDNF/NT-3 growth factors receptor | | | 0.1707 | 0.0359 |
| FLG-Hs00863478_g1 | Filaggrin | 0.7257 | 0.01555 | | |

D. Effect on Lipolysis of Human Adipose Tissue

Human white adipose tissue exerts a fundamental metabolic function by providing to other tissues of the organism energy molecules in the form of fatty acids released by the adipocyte lipolysis process. The adipocyte mobilizes its energy reserves by hydrolysis of triglycerides stored in fatty acids and glycerol. The fatty acids thus released in the blood can be used as a source of energy by other tissues.

The effect of passionflower hydrolysate on adipocyte lipolysis was evaluated by an assay of glycerol released during hydrolysis of triglycerides stored in mature human adipocytes cultured in a three-dimensional system.

a) Materials and Methods

Mature adipocytes, isolated from biopsies of subcutaneous adipose tissue from four normal-weight or overweight female donors, were incubated in the presence of passionflower hydrolysate for 4 hours at 37° C. Released glycerol was assayed using a colorimetric method, and the values obtained were normalized to amount of DNA. The results were compared statistically by means of one-way analysis of variance followed by Dunnett's test.

b) Results

The results are presented in the following table:

TABLE 3

| | Glycerol (normalized data; mean ± SD) | |
|---|---|---|
| Control | $1.00 \pm 0.0$ | |
| Passionflower hydrolysate 0.005% | $1.69 \pm 0.23$ | $p < 0.05$ |

The 0.005% passionflower hydrolysate significantly stimulated glycerol release, showing an activator effect on adipocyte lipolysis.

E. Anti-Tyrosinase Activity

Tyrosinase is a key enzyme in melanin synthesis. Specific inhibitors of this enzyme can lead to inhibition of melanin synthesis and thus cause depigmenting effects. The effect of passionflower hydrolysate was evaluated on the activity of tyrosinase extracted from human melanocytes (cell-free test).

a) Materials and Methods

Passionflower hydrolysate and the test standard (kojic acid) were brought together with the enzymatic extract (tyrosinase) and incubated on ice for 10 minutes. At the conclusion of incubation, the substrate L-DOPA (2 mM) was added and the samples were incubated for 1 hour at 37° C. Enzymatic activity was evaluated by colorimetry (reading of optical density at 540 nm). The results were expressed as a percentage of tyrosinase activity and compared statistically using Student's t-test.

b) Results

The results are presented in the following table:

TABLE 4

| | Tyrosinase activity (% of control) | p | $IC_{50}$ |
|---|---|---|---|
| Control | 100 | — | — |
| 0.0625 mM kojic acid | 95 | NS | 0.76 mM |
| 0.125 mM kojic acid | 93 | NS | |
| 0.25 mM kojic acid | 88 | $p < 0.05$ | |
| 0.5 mM kojic acid | 66 | $p < 0.001$ | |
| 1 mM kojic acid | 36 | $p < 0.001$ | |
| 0.005% passionflower hydrolysate | 101 | NS | 0.16% |
| 0.01% passionflower hydrolysate | 97 | NS | |
| 0.05% passionflower hydrolysate | 83 | $p < 0.05$ | |
| 0.1% passionflower hydrolysate | 70 | $p < 0.01$ | |
| 0.5% passionflower hydrolysate | 0 | $p < 0.001$ | |
| 1% passionflower hydrolysate | −3 | $p < 0.001$ | |

Passionflower hydrolysate inhibited in a clear and concentration-dependent manner the enzymatic activity of tyrosinase ($IC_{50}$=0.16%).

F. Protection Against Oxidative Stress

Oxidative stress, whether induced endogenously or exogenously (tobacco use, atmospheric pollution, UV radiation), is responsible for many skin disorders. Indeed, via the production of free radicals, oxidative stress can alter the various components of skin cells: proteins, lipids, nuclear and mitochondrial DNA. An antioxidant effect of passionflower hydrolysate was confirmed by first evaluating its ability to modulate the production of free radicals and second its protective effect against peroxidation of lipids in cells subjected to oxidative stress.

1. Effect on Production of Reactive Oxygen Species in Keratinocytes

The antioxidant action of passionflower hydrolysate on oxidative stress generated by hydrogen peroxide ($H_2O_2$) in keratinocytes was evaluated by measuring the amount of reactive oxygen species produced. This test is based on the use of a probe (DCFH-DA) that breaks down and fluoresces in contact with reactive oxygen species (ROS). The fluorescence emitted will be thus proportional to the amount of ROS produced by the cell in response to oxidative stress.

a) Materials and Methods

Normal human keratinocytes were preincubated for 24 hours in the presence of passionflower hydrolysate or the reference molecules: 10 µM quercetin or 500 µM vitamin C. The cells were then incubated for 1 hour in the presence of the probe DCFH-DA and then treated with 100 µM $H_2O_2$ for 20 minutes, still in the presence of passionflower hydrolysate or the reference molecules. The ROS assay was carried out by measuring the fluorescence emitted. The results were normalized to the number of living cells determined using a neutral red uptake assay carried out in parallel. The amount of ROS emitted is thus expressed as fluorescence density (DFU)/optical density resulting from the neutral red assay ($OD_{540}$). The results were statistically analyzed by one-way analysis of variance followed by Tukey's test.

b) Results

The results are presented in the following table:

TABLE 5

|  | Amount of ROS DFU/$OD_{540}$ (mean ± standard deviation) | Increase relative to the control | Inhibition relative to the $H_2O_2$ control |
|---|---|---|---|
| Control | 62132.821 ± 10278.568 |  |  |
| $H_2O_2$ control (stress) | 287593.309 ± 45380.022 | +363% p < 0.001 |  |
| Quercetin (reference) | 84549.570 ± 9476.724 |  | −71% p < 0.001 |
| Vitamin C (reference) | 35997.820 ± 10389.067 |  | −87% p < 0.001 |
| 0.01% passionflower hydrolysate | 98585.727 ± 7972.591 |  | −66% p < 0.001 |
| 0.05% passionflower hydrolysate | 56063.620 ± 3540.141 |  | −81% p < 0.001 |
| 0.1% passionflower hydrolysate | 45893.532 ± 3120.083 |  | −84% p < 0.001 |

Passionflower hydrolysate strongly and in a highly significant manner inhibited the production of ROS induced by $H_2O_2$ stress.

2. Protective Effect on Lipid Peroxidation

The protective effect of passionflower hydrolysate on lipid peroxidation was evaluated in UV-irradiated Jurkat cells.

a) Materials and Methods

Jurkat cells were incubated for 45 minutes in the presence or absence of passionflower hydrolysate or the reference (50 µM BHT) and in the presence of the fluorescent probe specific for the measurement of lipid peroxides (C11-fluorine). This fluorescent probe is a lipid analog that integrates into membranes and whose fluorescence intensity decreases when peroxidized. The cells were then irradiated by UV (UVB 240 mJ/$cm^2$+UVA 3.5 J/$cm^2$) in the presence of passionflower hydrolysate or the reference. At the conclusion of the irradiation, the cells were incubated for 30 minutes at 37° C. prior to being analyzed by flow cytometry. The fluorescence intensity results obtained were expressed as a % of the irradiated control.

b) Results

The results are presented in the following table:

TABLE 6

|  | Amount of lipid peroxides (% of the irradiated control) | Protection (%) |
|---|---|---|
| Control (not irradiated) | 46 | 100 |
| Irradiated (UV) control | 100 | 0 |
| UV + BHT | 83 | 31 |
| UV + 0.05% passionflower hydrolysate | 87 | 24 |

The 0.05% passionflower hydrolysate protected the cells from lipid peroxidation induced by UV irradiation (24% protection).

The invention claimed is:

1. A cosmetic, dermatological and pharmaceutical composition comprising a peptide and sugar extract of passionflower seeds, as active agent, and a suitable excipient, wherein the peptide and sugar extract is obtained by enzymatic hydrolysis of passionflower seeds, in the presence of at least one acid protease and at least one carbohydrase, wherein the peptide and sugar extract comprises 20% to 70% by weight peptides and 20% to 60% by weight sugars.

2. The composition of claim 1, wherein the passionflower is *Passiflora incarnata* or *Passiflora edulis*.

3. The composition according to claim 1, wherein in the peptide and sugar extract the peptides have a size less than 3500 Da.

4. The composition according to claim 1, wherein in the peptide and sugar extract the weight ratio of peptides/sugars is greater than 0.75.

5. The composition according to claim 4, wherein the peptide and sugar extract comprises 30% to 65% by weight peptides.

6. The composition according to claim 4, wherein the peptide and sugar extract comprises typically 55% by weight peptides.

7. The composition according to claim 4, wherein the peptide and sugar extract comprises 30% to 55% by weight sugars.

8. The composition according to claim 4, wherein the peptide and sugar extract comprises typically 40% by weight sugars.

9. The composition according to claim 1, comprising 0.001% to 10% by weight of said peptide and sugar extract of passionflower seeds, the weight of the extract being expressed in dry extract, in relation to the total weight of the composition.

10. The composition according to claim 1, comprising 0.01% to 5% by weight of said peptide and sugar extract of passionflower seeds, the weight of the extract being expressed in dry extract, in relation to the total weight of the composition.

11. The composition according to claim 1, further comprising one other active agent, in addition to the peptide and sugar extract of passionflower seeds, said one other active agent being advantageously selected from:
emollients, moisturizing active agents, keratin-synthesis activators, keratoregulators, keratolytics, agents that restructure the cutaneous barrier (activators of synthesis of cutaneous lipids), peroxisome proliferator-activated receptor (PPAR) agonists, RXR or LXR agonists, sebum-regulating agents, anti-irritant agents, soothing agents, anti-inflammatory agents, antioxidants and anti-aging agents, depigmenting or hypodepigmenting agents, pigmenting agents, lipolytic agents or lipogenesis inhibitors or anti-cellulite or reducing agents, inorganic or organic sun filters and screens, antifungal compounds, preservatives, antibacterial agents, prebiotics and probiotics, antibiotics, immunomodulators;
plant extracts; and
oxazolines.

12. A process for preparing a peptide and sugar extract of passionflower seeds, comprising at least one enzymatic hydrolysis of passionflower seeds step in the presence of at least one "acid" protease and at least one carbohydase, wherein the peptide and sugar extract comprises 20% to 70% by weight peptides and 20% to 60% by weight sugars.

13. The process according to claim 12, wherein passionflower seeds are *Passiflora incarnata* seeds or *Passiflora edulis* seeds.

14. The process according to claim 12, comprising the following successive steps:
a) dispersion in an aqueous phase of grinded passionflower seeds, then
b) enzymatic treatment, by adding "said" at least one "acid" protease and at least one carbohydase, of the aqueous dispersion obtained in step a), then
c) if need be, heat treatment in order to denature the enzymes, and
d) collection of the peptide and sugar extract at the conclusion of step b) or c).

15. The process according to claim 14, wherein the enzymatic treatment successively comprises a step b1) of adding a carbohydase, then a step b2) of adding said at least one acid protease.

16. The process according to claim 15, wherein the enzymatic treatment successively comprises a step b1) of adding a carbohydase, selected from pectinases, cellulases, arabanases, hemicellulases, xylanases and β-glucanases.

17. The process according to claim 14, wherein prior to step a) the seeds are defatted.

18. The process according to claim 14, comprising an additional step, between steps b), or if need be c), and d) of filtration or centrifugation, optionally followed by ultrafiltration, diafiltration or nanofiltration.

19. The process according to claim 18, comprising a step of 15 kDa ultrafiltration.

20. A peptide and sugar extract of passionflower seeds obtained by a process comprising at least one enzymatic hydrolysis of passionflower seeds step in the presence of at least one "acid" protease and at least one carbohydase, wherein the peptide and sugar extract of passionflower seeds contains 20% to 70% by weight peptides and 20% to 60% by weight sugars.

21. A peptide and sugar extract according to claim 20, wherein the passionflower seeds are *Passiflora incarnata* seeds or *Passiflora edulis* seeds, advantageously *Passiflora edulis* seeds.

22. The extract according to claim 20, containing 30% to 65% by weight peptides and 30% to 55% by weight sugars.

23. The extract according to claim 20, containing typically 55% by weight pepteides and typically 40% by weight sugars.

24. A method for preventing and for treating:
disorders or pathological conditions of the skin and/or the mucous, membranes and/or the skin appendages,
vascular disorders,
adipose tissue modifications,
oxidative stress,
comprising the administration to a person in need thereof of an extract according to claim 20.

25. A cosmetic care process for the skin and/or the skin appendages and/or the mucous membranes, with a view to improving the condition and/or appearance thereof, comprising administering a cosmetic composition as defined according to claim 1.

26. A method for preventing and for treating:
disorders or pathological conditions of the skin and/or the mucous, membranes and/or the skin appendages,
vascular disorders,
adipose tissue modifications,
oxidative stress,
comprising the administration to a person in need thereof of a composition according to claim 1.

27. A cosmetic care process for the skin and/or the skin appendages and/or the mucous membranes, with a view to improving the condition and/or appearance thereof, comprising administering an extract as defined according to claim 20.

28. A cosmetic care process for the skin and/or the skin appendages and/or the mucous membranes, with a view to improving the condition and/or appearance thereof, comprising administering an extract as defined according to claim 20.

29. The composition according to claim 4, wherein in the peptide and sugar extract the weight ratio of peptides/sugars is between 1 and 2.

* * * * *